(12) United States Patent
Paz et al.

(10) Patent No.: US 10,837,955 B2
(45) Date of Patent: Nov. 17, 2020

(54) CLOT MITIGATING PROBE FOR BLOOD ANALYZING INSTRUMENT

(71) Applicant: Instrumentation Laboratory Company, Bedford, MA (US)

(72) Inventors: Roman Paz, Watertown, MA (US); Brian Walker, Fitchburg, MA (US); Zachary Hastings, Bedford, MA (US); Michael Aschettino, Marlborough, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 0 days.

(21) Appl. No.: 15/861,251

(22) Filed: Jan. 3, 2018

(65) Prior Publication Data

US 2018/0196029 A1    Jul. 12, 2018

Related U.S. Application Data (60) Provisional application No. 62/444,628, filed on Jan. 10, 2017.

(51) Int. Cl.
*G01N 33/49* (2006.01)
*G01N 33/86* (2006.01)
(Continued)

(52) U.S. Cl.
CPC .............. *G01N 33/49* (2013.01); *G01N 33/86* (2013.01); *G01N 35/1016* (2013.01); *A61B 5/150755* (2013.01); *G01N 2035/1018* (2013.01)

(58) Field of Classification Search
CPC .............. G01N 33/86; G01N 35/1016; G01N 2035/1018; G01N 2001/2288; G01N 2035/1053; G01N 33/49; A61B 5/150755
(Continued)

(56) References Cited

U.S. PATENT DOCUMENTS 4,340,067 A * 7/1982 Rattenborg ........ A61B 5/15003
600/576
4,545,382 A   10/1985 Higgins
(Continued)

FOREIGN PATENT DOCUMENTS

CN   203736591 U   7/2014
CN   204468877 U   7/2015
(Continued)

OTHER PUBLICATIONS

International Preliminary Report on Patentability issued in the corresponding International Application No. PCT/US2018/12200, dated Jul. 25, 2019; 9 pages.
(Continued)

*Primary Examiner* — Robert R Raevis
(74) *Attorney, Agent, or Firm* — Burns & Levinson, LLP; Joseph P. Quinn (57) ABSTRACT

Aspects of the present disclosure include a titration probe that mitigate the occurrences of titration probe clots. A bar such as segment of music wire, is extended across the tip of a titration probe and attached at both ends to the titration probe. The bar is configured to catch clots and prevent the clots from being collected along with a blood sample to be analyzed. The bar effectively reduces the cross sectional area of the titration probe tip.

7 Claims, 9 Drawing Sheets

(51) Int. Cl.
  *G01N 35/10*   (2006.01)
  *A61B 5/15*   (2006.01)
(58) Field of Classification Search
  USPC .............. 73/864.81, 864.23, 864.01–864.21,
        73/864.44, 864.73, 864.74; 422/75–77,
        422/501, 513, 527, 534
  See application file for complete search history.

(56) References Cited

U.S. PATENT DOCUMENTS

| | | | |
|---|---|---|---|
| 5,078,677 A | | 1/1992 | Gentelia |
| 7,380,615 B1 * | | 6/2008 | Vanearden ............... A01B 1/16 |
| | | | 111/92 |
| 9,702,791 B2 * | | 7/2017 | Jenkins ................... G01N 1/02 |
| 2003/0136204 A1 * | | 7/2003 | Bergquist ................. G01N 1/08 |
| | | | 73/864.44 |
| 2003/0209451 A1 | | 11/2003 | Dineen |

FOREIGN PATENT DOCUMENTS

| | | |
|---|---|---|
| CN | 105699677 A | 6/2016 |
| JP | S53-039488 U | 4/1978 |
| JP | H11-237378 A | 8/1999 |
| WO | 9635938 | 11/1996 |

OTHER PUBLICATIONS

International Search Report and Written Opinion in the corresponding International Application No. PCT/US18/12200, dated Apr. 5, 2018; 15 pages.
First Office Action issued in corresponding Chinese application No. 201880006495.5, dated Dec. 30 2019 (8 pages), and English translation thereto (14 pages).
Office Action dated Jun. 2, 2020 issued in corresponding Japanese application No. 2019-529856, 4 pages and English translation thereof, 5 pages.
Communication under Rule 71(3) EPC dated May 29, 2020 issued in corresponding European application No. 18701829.6 27 pages.
Song et al., On-Chip Titration of an Anticoagulant Argatroban and Determination of the Clotting Time within Whole Blood or Plasma Using a Plug-Based Microfluidic System, Anal. Chem, vol. 78, No. 14, Jul. 15, 2006, pp. 4839-4849.
Examiner Requisition issued in corresponding Canadian application No. 3,046,242, dated Aug. 26 2020 (6 pages).
Examination Report No. 1 issued in corresponding Australian application No. 2018207048, dated Oct. 1, 2020 (5 pages).

* cited by examiner

| Date | | 1-Nov | | 2-Nov | | Bar+Asp.+Side Hole+Purge | | 3-Nov | | 4-Nov | | Bar+Asp.+Side Hole No Purge | |
|---|---|---|---|---|---|---|---|---|---|---|---|---|---|
| | | Control | Test | Control | Test | Control | Bar probe | Control | Test | Control | Test | Control | Bar probe |
| Configuration | | | | | | | | | | | | | |
| Heparin Setting | | | | | | 0.85/45/90 | | | | | | 0.85/45/90 | |
| # PAKs Total | | 21 | 11 | 29 | 12 | 39 | 12 | 28 | 12 | 25 | 12 | 38 | 13 |
| Sample Size | | 489 | 379 | 599 | 562 | 1088 | 941 | 579 | 567 | 475 | 559 | 1054 | 1126 |
| Sampled Aborted % | | 24% | 20% | 16% | 16% | 20% | 18% | 14% | 19% | 16% | 20% | 15% | 19% |
| Sample Not Detected % | | 21% | 15% | 15% | 14% | 18% | 14% | 13% | 17% | 15% | 18% | 14% | 18% |
| Insufficient Sample % | | 3% | 5% | 1% | 2% | 2% | 3% | 1% | 2% | 1% | 1% | 1% | 2% |
| Insufficient Sample for COOX % | | 0% | 1% | 0% | 1% | 0% | 1% | 0% | 0% | 0% | 0% | 0% | 0% |
| Total Clot of Samples % | | 4% | 3% | 6% | 3% | 5% | 3% | 6% | 2% | 8% | 6% | 7% | 4% |
| Clot Pattern 1 (Drift) % | | 38% | 55% | 35% | 38% | 36% | 44% | 43% | 57% | 29% | 38% | 36% | 43% |
| Clot Pattern 2 (Slope) % | | 0% | 0% | 5% | 0% | 3% | 0% | 0% | 0% | 3% | 0% | 1% | 0% |
| Clot Pattern 3 (Fluidic) % | | 62% | 27% | 51% | 50% | 55% | 41% | 49% | 29% | 55% | 47% | 52% | 41% |
| Clot Pattern 4 (COOX only) % | | 0% | 18% | 8% | 13% | 5% | 15% | 9% | 14% | 13% | 16% | 11% | 15% |
| Cartridge Rejection of Total Samples % | | 2.0% | 0.0% | 2.3% | 0.0% | 2.2% | 0.0% | 2.2% | 0.2% | 3.2% | 0.2% | 2.7% | 0.2% |
| Cartridge Rejection of Total Clots % | | 48% | 0% | 38% | 0% | 41% | 0% | 37% | 7% | 39% | 3% | 38% | 4% |
| Cartridge Rejection of Clot Pattern 3 % | | 69% | 0% | 74% | 0% | 72% | 0% | 76% | 25% | 48% | 7% | 61% | 11% |
| Cartridge Rejection of Total PAKs % | | 48% | 0% | 48% | 0% | 62% | 0% | 46% | 8% | 60% | 8% | 74% | 15% |
| Sampled Aborted | | 118 | 76 | 97 | 90 | 215 | 166 | 82 | 109 | 74 | 110 | 156 | 219 |
| Sample Not Detected | | 101 | 56 | 90 | 76 | 191 | 132 | 77 | 98 | 71 | 101 | 148 | 199 |
| Insufficient Sample | | 16 | 18 | 6 | 11 | 22 | 29 | 4 | 10 | 3 | 8 | 7 | 18 |
| Insufficient Sample for COOX | | 1 | 2 | 1 | 3 | 2 | 5 | 1 | 1 | 0 | 1 | 1 | 2 |
| Total Clots Detected | | 21 | 11 | 37 | 16 | 58 | 27 | 35 | 14 | 38 | 32 | 73 | 46 |
| Clot Pattern 1 (Drift) | | 8 | 6 | 13 | 6 | 21 | 12 | 15 | 8 | 11 | 12 | 26 | 20 |
| Clot Pattern 2 (Slope) | | 0 | 0 | 2 | 0 | 2 | 0 | 0 | 0 | 1 | 0 | 1 | 0 |
| Clot Pattern 3 (Fluidic) | | 13 | 3 | 19 | 8 | 32 | 11 | 17 | 4 | 21 | 15 | 38 | 19 |
| Clot Pattern 4 (COOX only) | | 0 | 2 | 3 | 2 | 3 | 4 | 3 | 2 | 5 | 5 | 8 | 7 |
| Sensor Disabled from All Clots | | 0 | 0 | 1 | 0 | 1 | 0 | 0 | 1 | 1 | 0 | 1 | 0 |
| Cartridge Rejected Total | | 10 | 0 | 14 | 0 | 24 | 0 | 13 | 1 | 15 | 1 | 28 | 2 |
| Pattern 3 | | 9 | 0 | 14 | 0 | 23 | 0 | 13 | 1 | 10 | 1 | 23 | 2 |
| Pattern 1 | | 0 | 0 | 0 | 0 | 0 | 0 | 0 | 0 | 3 | 0 | 3 | 0 |
| Cartridge error | | 1 | 0 | 0 | 0 | 1 | 0 | 0 | 0 | 2 | 0 | 2 | 0 |

FIG. 19

CLOT MITIGATING PROBE FOR BLOOD ANALYZING INSTRUMENT

CROSS REFERENCE TO RELATED APPLICATIONS

This application claims priority to and benefit of U.S. Provisional Application No. 62/444,628 filed on Jan. 10, 2017, the entire content of which is incorporated by reference herein for all purposes.

FIELD OF TECHNOLOGY

The present disclosure relates to the field blood sampling apparatus and more particularly to titration probes.

BACKGROUND

Previously existing titration probes for acquiring whole blood samples have been susceptible to blockage by clots, particularly at the probe distal end. Blood clots and other accumulations of materials that collect around a blockage can become free and contaminate a collected sample. This can interfere with testing of the collected sample and may result in inaccurate test results.

SUMMARY

An aspect of the present disclosure includes an analyzer probe for titrating a whole blood sample. The probe includes an elongated body, such as a tubular body, defining a longitudinal axis extending between proximal and distal ends, a titration channel defined by the elongated body and extending therethrough along the longitudinal, a primary opening to the titration channel defined at the distal end of the elongated body, and a bar extending across the titration channel along a first transverse axis, wherein the bar is configured to temporarily split a cross-sectional flow path of the titration channel at a first distal region thereof. An interface is defined toward the proximal end of the elongated body for operatively coupling the probe with a blood analyzer, whereby a blood sample may be drawn in through the proximal opening, through the titration channel and into the blood analyzer for analysis. According to an aspect of the present disclosure, the primary opening is aligned with the longitudinal axis. The bar is configured to bisect the cross-sectional flow-path of the titration channel at the first distal region.

In an illustrative embodiment, the analyzer probe also includes at least one secondary opening to the titration channel defined through a side wall of the elongated body at a second distal region of the titration channel proximal to the first distal region. In one implementation, the secondary opening is defined along a second transverse axis perpendicular to the first transverse axis. According to an aspect of the present disclosure, the secondary opening may be smaller than the primary opening.

Another aspect of the present disclosure includes a method for manufacturing an analyzer probe. The method includes providing a probe comprising an elongated body defining a longitudinal axis extending between proximal and distal ends, a titration channel defined by the elongated body and extending therethrough along the longitudinal axis, and a primary opening to the titration channel defined at the distal end of the elongated body. The method also includes defining a first set of apertures through the elongated body along a first transverse axis and threading a rod or wire material through the first set of apertures so as to define a bar extending across the titration channel along the first transverse axis. The bar is configured to split a cross-sectional flow path of the titration channel at a first distal region thereof. The method also includes attaching the rod or wire material to the elongated body at each of the apertures in the first set of apertures.

According to an aspect of the present disclosure, the method also includes defining at least one secondary opening to the titration channel through a side wall of the elongated body at a second distal region of the titration channel proximal to the first distal region. The secondary opening is defined along a second transverse axis perpendicular to the first transverse axis. In an illustrative embodiment, the secondary opening is smaller than the primary opening. The method also includes removing any portion the rod or wire material protruding past the apertures and smoothing fused regions thereof so as to form a smooth and continuous surface of the elongated body.

Another aspect of the present disclosure includes a method of titrating a whole blood sample. The method includes providing a probe interfaced with a blood analyzer. The probe includes an elongated body defining a longitudinal axis extending between proximal and distal ends, a titration channel defined by the elongated body and extending therethrough along the longitudinal axis, a primary opening to the titration channel defined at the distal end of the elongated body, and a bar extending across the titration channel along a first transverse axis. The bar is configured to split a cross-sectional flow path of the titration channel at a first distal region thereof. An interface is defined toward the proximal end of the elongated body for operatively coupling the probe with a blood analyzer. The method also includes inserting the probe into a target region; and using the probe to draw a whole blood sample from the target region in through the proximal opening, through the titration channel and into the blood analyzer for analysis. In an illustrative embodiment, the method also includes defining at least one secondary opening to the titration channel through a side wall of the elongated body at a second distal region of the titration channel proximal to the first distal region. In an illustrative embodiment, the secondary opening is defined along a second transverse axis perpendicular to the first transverse axis and is smaller than the primary opening.

BRIEF DESCRIPTION OF THE DRAWINGS

FIG. 17 is a table of test results for an analyzer probe according to aspect of the present disclosure.

DETAILED DESCRIPTION

Aspects of the present disclosure include titration probe design aspects that mitigate the occurrence of titration probe clots.

Figure 7:
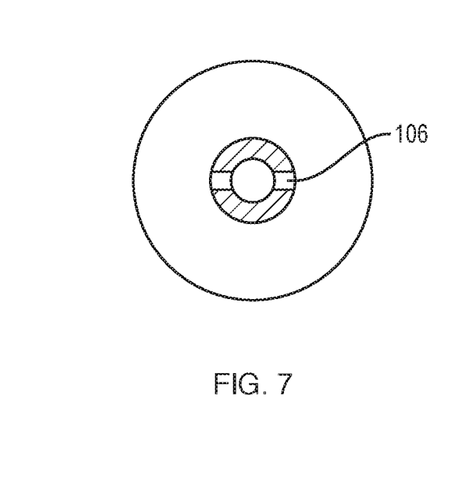
FIG. 7 is a cross sectional view of a distal portion of the analyzer probe as shown in FIG. 4 at a section plane labeled 7-7.
Figure 8:
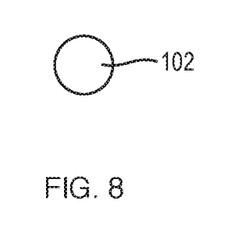
FIG. 8 is an end view of a pin for bisecting a titration channel according to an aspect of the present disclosure.
Figure 9:
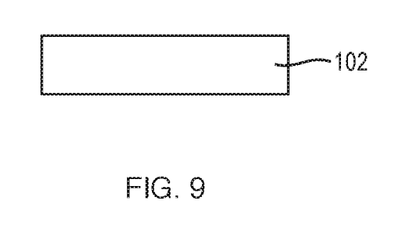
FIG. 9 is a side view of a pin for bisecting a titration channel according to an aspect of the present disclosure.
Figure 10:
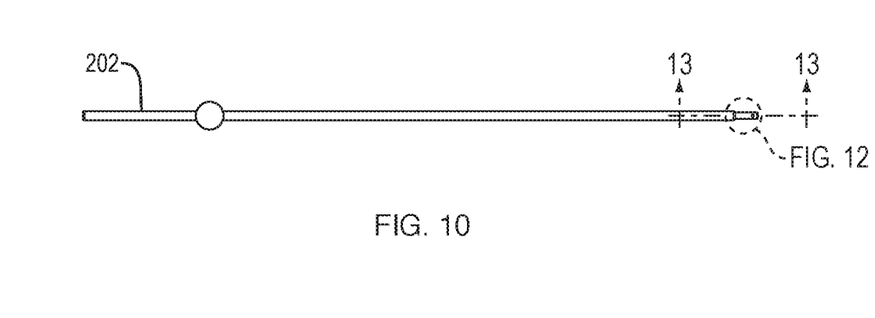
FIGS. 10 and 11 are side view drawings of an analyzer probe according to an aspect of the present disclosure.
Figure 11:
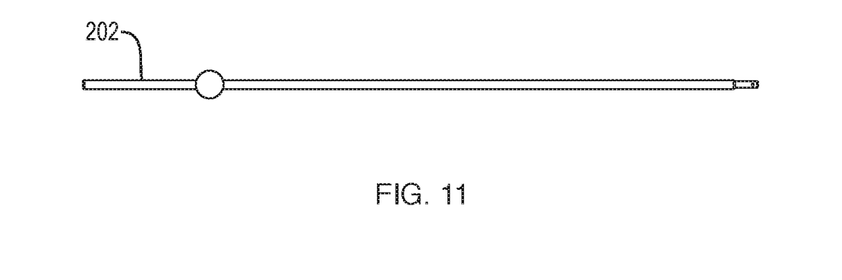
Figure 12:
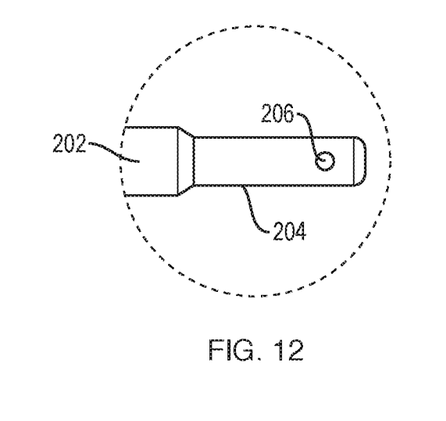
FIG. 12 is a side view detail drawing of a distal portion of the analyzer probe shown in FIG. 10.
Figure 13:
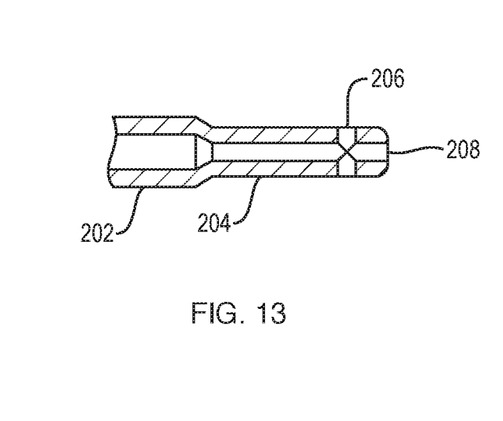
FIG. 13 is a cross sectional view of a distal portion of the analyzer probe shown in FIG. 10 at a section plane labeled 13-13.

Referring to FIGS. 1-7, according to an aspect of the present disclosure a bar 102 (best seen in FIGS. 1, 6, 8 and 9), such as segment of music wire, is extended across the tip of a titration probe 104 and welded at both ends to the titration probe 104. The bar 102 is configured to catch clots and prevent the clots from being collected with along with the blood sample. FIGS. 8-9 show an illustrative embodiment of the bar 102 according to an aspect of the present disclosure before it is installed in the titration probe 104.

Figure 1:
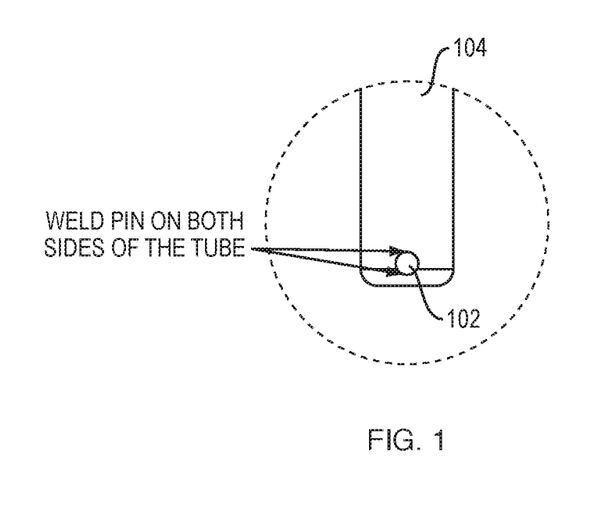
FIG. 1 is a front view detail drawing showing a distal portion of an analyzer probe according to an aspect of the present disclosure.

The bar 102 effectively reduces the inside diameter of the titration probe 104 down to smaller sections. In an illustrative embodiment, the inside diameter of the titration probe tip is effectively cut in half.

Previously existing titration probes also may become blocked and are unable to collect samples when the probe is bottomed out, i.e., wherein the probe's distal opening are pushed against a surface.

According to another aspect of the present disclosure, the titration probe 104 includes, two side holes 106 (best seen in FIGS. 2 and 7) proximal to the bar 104.

Figure 2:
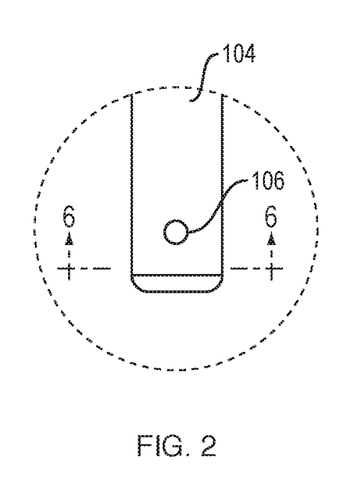
FIG. 2 is a side view detail drawing showing a distal portion of an analyzer probe according to an aspect of the present disclosure.
Figure 3:
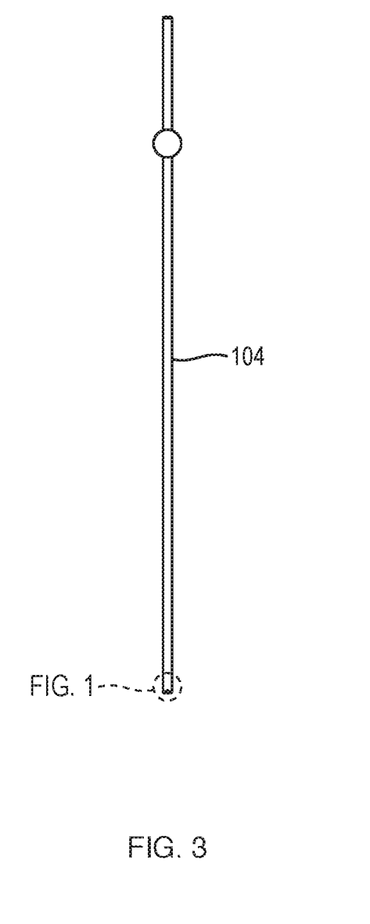
FIG. 3 is a front view drawing of an analyzer probe according to an aspect of the present disclosure.
Figure 4:
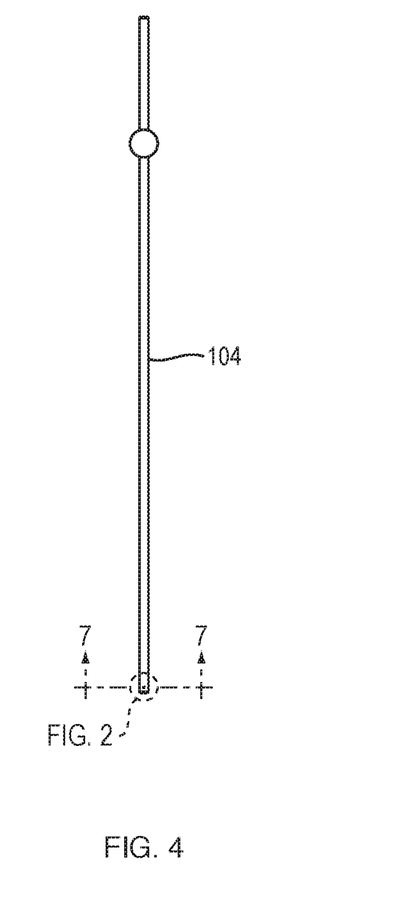
FIG. 4 is a side view drawing of an analyzer probe according to an aspect of the present disclosure.
Figure 5:
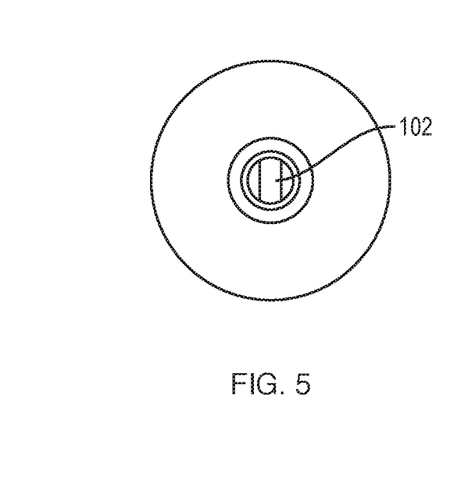
FIG. 5 is an end view drawing of an analyzer probe according to an aspect of the present disclosure.
Figure 6:
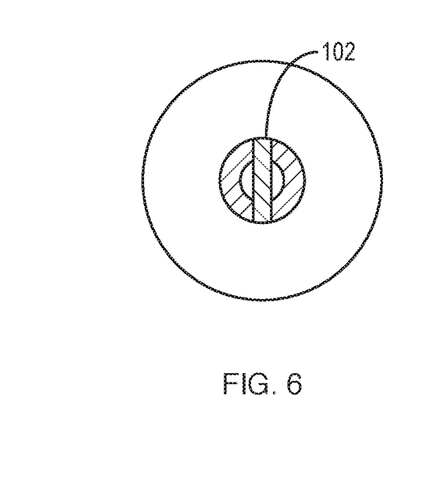
FIG. 6 is a cross sectional view of a distal portion of the analyzer probe as shown in FIG. 2 at a section plane labeled 6-6.

The side holes 106 provide a fluid pathway that allows a user to pull samples into the system even when the titration probe 104 is bottomed out against a surface, and even when the distal end of the titration probe 104 is blocked by a sample accumulation or a clot, for example. By redirecting sample flow to the side holes 106, the sample accumulation or a clot is not forced further into the titration probe 104, and may simply be wiped off once the titration probe is retracted back into a test instrument, for example.

FIGS. 10-13 illustrate a swaged tip titration probe 202 according to another aspect of the present disclosure. According to this aspect of the present disclosure, the outside diameter of a distal tip 204 of the swaged tip titration probe 202 is swaged down until the inside diameter of the tube is 0.010".

Advantageously, the swaged tip titration probe 202 easily manufactured, inexpensive, and capable of limiting the particle size allowed to enter a test system. According to another aspect of the present disclosure, the distal tip 204 includes side holes 206 for additional aspiration to allow sample collection when the distal opening is blocked by the bottoming the probe or by foreign material that is pulled through the front of our probe, blocking its distal inlet 208.

Figure 14:
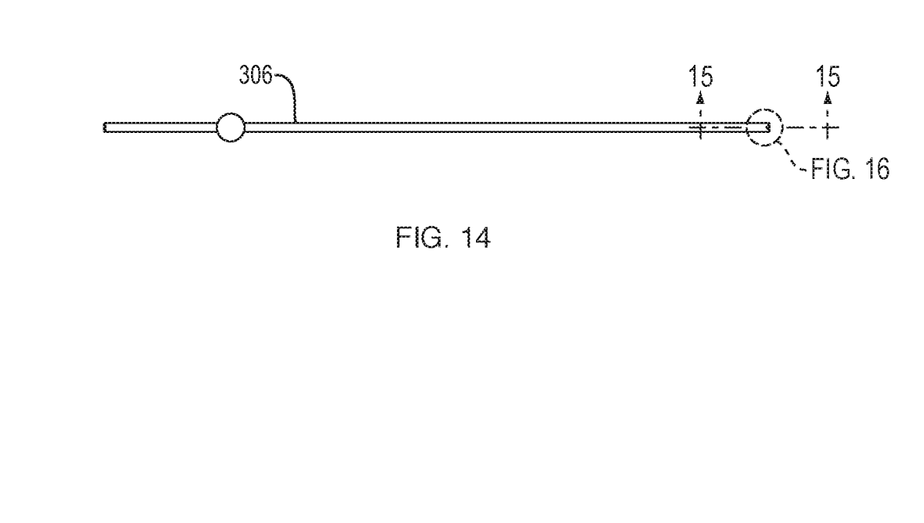
FIG. 14 is a side view drawing of an analyzer probe according to an aspect of the present disclosure.
Figure 15:
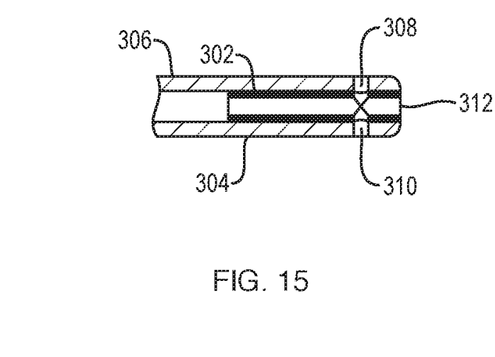
FIG. 15 is a cross sectional view of a distal portion of the analyzer probe shown in FIG. 14 at a section plane labeled 15-15.
Figure 16:
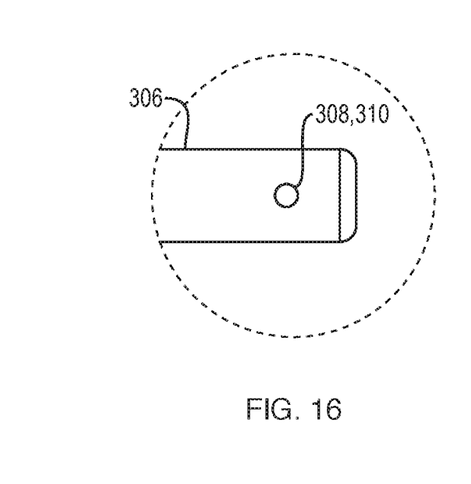
FIG. 16 is a side view detail drawing of a distal portion of the analyzer probe shown in FIG. 14.

FIGS. 14-16 illustrate another aspect of the present disclosure in which an insert 302 is installed in the distal tip 304 of a titration probe 306 to reduce the inside diameter of the distal tip 304. In an illustrative embodiment, different inserts 302 with various different inside diameters can be used for particular probe applications, for example.

In the embodiment shown in FIGS. 14-16, an insert 302 having an inside diameter of 0.010" is installed in the distal tip 304 of the titration probe 306 to limit unwanted foreign material from being drawn into a test system.

According to another aspect of the present disclosure, the distal tip 304 includes side holes 308 and the insert 302 includes side holes 310. The side holes 308 in the distal tip 304 are aligned with the side holes 301 in the insert 302 for additional aspiration to allow sample collection when the distal opening is blocked by the bottoming the probe or by foreign material that is pulled through the front of our probe, blocking its distal inlet 312, for example.

According to an aspect of the present disclosure, an analyzer probe for titrating a whole blood sample includes an elongated body defining a longitudinal axis extending between proximal and distal ends and a titration channel defined by the elongated body and extending therethrough along the longitudinal axis. A primary opening to the titration channel is defined at the distal end of the elongated body. A bar extends across the titration channel along a first transverse axis. The bar is configured to temporarily split a cross-sectional flow path of the titration channel at a first distal region thereof. An interface is defined toward the proximal end of the elongated body for operatively coupling the probe with a blood analyzer, whereby a blood sample may be drawn in through the proximal opening, through the titration channel and into the blood analyzer for analysis. The elongated body is tubular and the primary opening is aligned with the longitudinal axis. The bar is configured to bisect the cross-sectional flow-path of the titration channel at the first distal region.

According to an aspect of the present disclosure, the analyzer probe also includes at least one secondary opening to the titration channel defined through a side wall of the elongated body at a second distal region of the titration channel proximal to the first distal region. The secondary opening(s) is/are defined along a second transverse axis perpendicular to the first transverse axis. In an illustrative embodiment secondary openings are smaller than the primary opening.

FIG. 17 shows the results for the analyzer probe described above with reference to FIGS. 1-9. The results demonstrate that the titration probe 104 can successfully prevent clots from entering a test system. This provides a safety margin if users are to perform testing of badly clotted samples, for example and can help alleviate the risk of a cartridge rejection or incorrect sample result seen from a poorly prepared sample.

Figure 18:
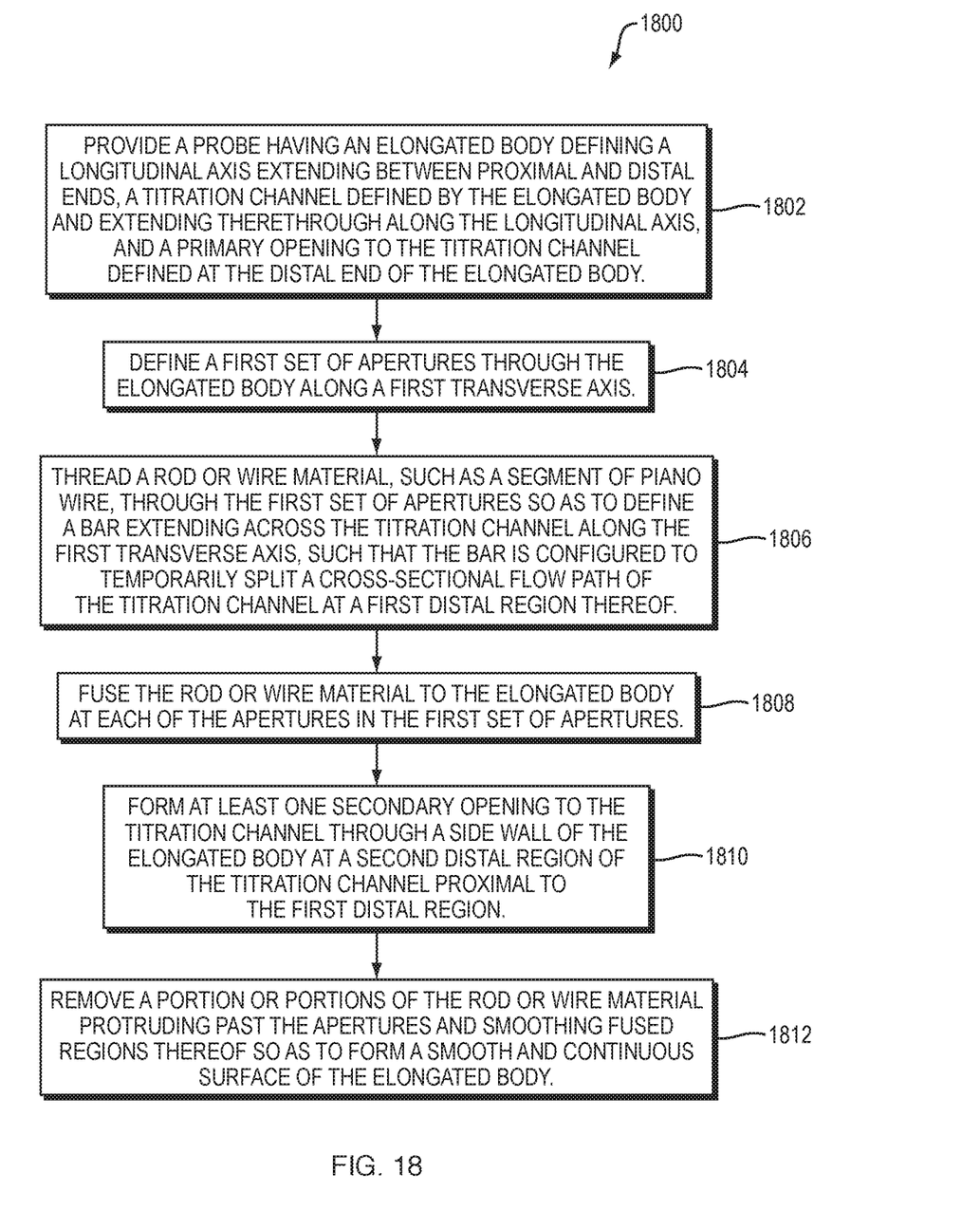
FIG. 18 is a process flow diagram showing a method for manufacturing an analyzer probe according to an aspect of the present disclosure.

Referring to FIG. 18, an aspect of the present disclosure includes a method 1800 for manufacturing an analyzer probe. At block 1802, the method includes providing a probe having an elongated body defining a longitudinal axis extending between proximal and distal ends, a titration channel defined by the elongated body and extending therethrough along the longitudinal axis, and a primary opening to the titration channel defined at the distal end of the elongated body.

At block 1804, the method includes defining a first set of apertures through the elongated body along a first transverse axis. At block 1806, the method includes threading a rod or wire material, such as a segment of piano wire, through the first set of apertures so as to define a bar extending across the titration channel along the first transverse axis, such that the bar is configured to temporarily split a cross-sectional flow path of the titration channel at a first distal region thereof. At block 1808, the method includes attaching the rod or wire material to the elongated body at each of the apertures in the first set of apertures. The attaching may be performed by welding or fusing the rod or wire material to the elongated body, for example.

At block 1810, the method includes forming at least one secondary opening to the titration channel through a side wall of the elongated body at a second distal region of the titration channel proximal to the first distal region. At block 1812, the method includes removing any portion the rod or wire material protruding past the apertures and smoothing fused regions thereof so as to form a smooth and continuous surface of the elongated body.

Figure 19:
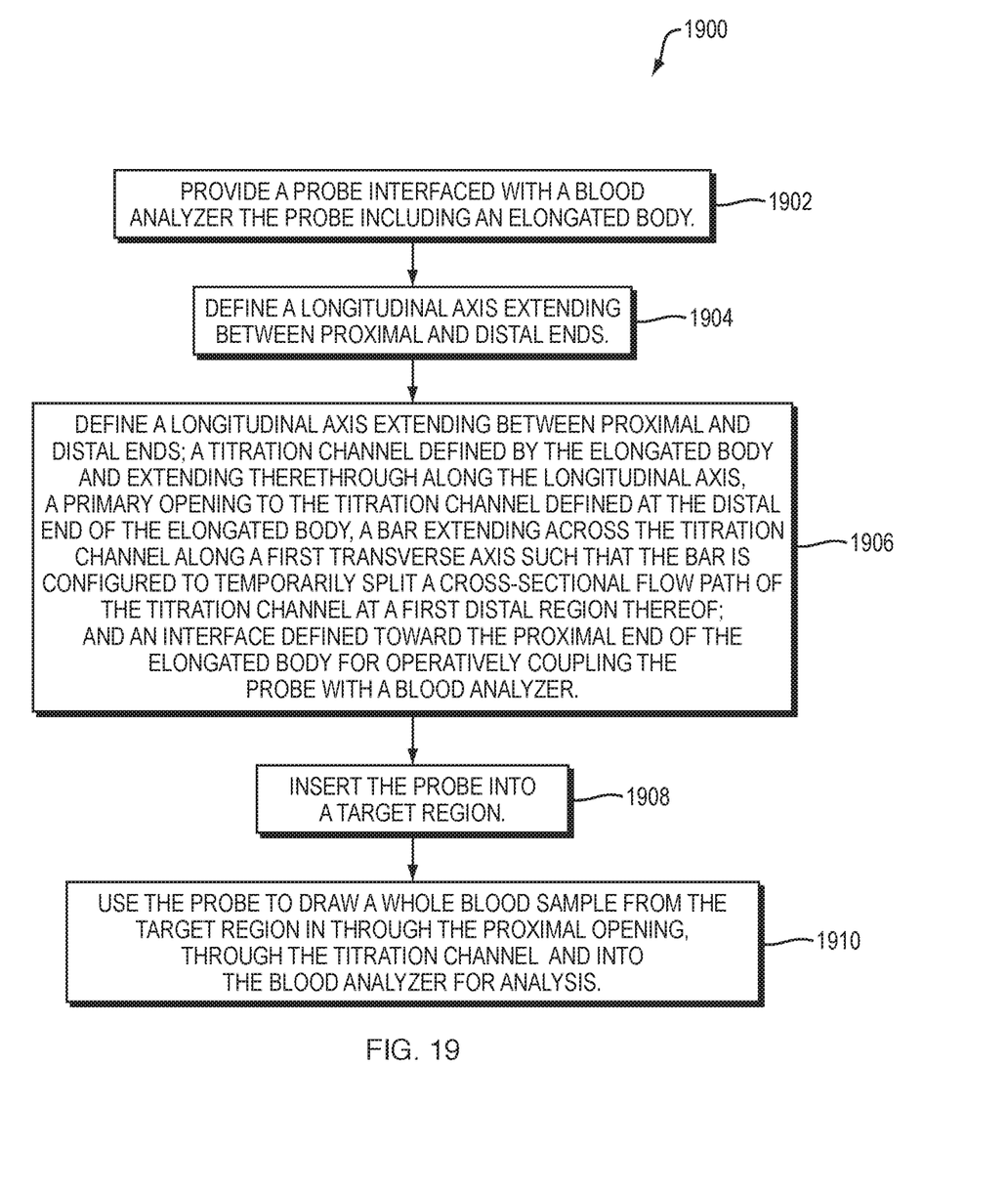
FIG. 19 is a process flow diagram showing a method for titrating a whole blood sample according to an aspect of the present disclosure.

Referring to FIG. 19, an aspect of the present disclosure includes a method 1900 for titrating a whole blood sample. At block 1902, the method includes providing a probe interfaced with a blood analyzer the probe including an elongated body. At block 1904, the method includes defining a longitudinal axis extending between proximal and distal ends; a titration channel defined by the elongated body and extending therethrough along the longitudinal axis, a primary opening to the titration channel defined at the distal end of the elongated body, a bar extending across the titration channel along a first transverse axis such that the bar is configured to temporarily split a cross-sectional flow path of the titration channel at a first distal region thereof; and an interface defined toward the proximal end of the elongated body for operatively coupling the probe with a blood analyzer. At block 1906, the method includes inserting the probe into a target region. At block 1908, the method includes using the probe to draw a whole blood sample from the target region in through the proximal opening, through the titration channel and into the blood analyzer for analysis.

The foregoing description of embodiments is intended to provide illustration and description but is not intended to be exhaustive or to limit the invention to the precise form disclosed. Modifications and variations are possible in light of the above teachings or may be acquired from practice of the invention.

No element, act, or instruction used herein should be construed as critical or essential to the invention unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A probe for mitigating occurrences of probe clots in a whole blood sample; the probe comprising:
   an elongated body defining a longitudinal axis extending between a proximal and a distal end, said proximal or distal end comprising a tip,
   the elongated body further defining a channel extending along the longitudinal axis;
   a primary opening to the channel defined at the distal end of the elongated body;
   an elongate member extending across from the tip of the probe's elongated body and configured to reduce the cross sectional area of the probe tip, wherein the elongate member is contoured to catch clots and preventing the clots from being collected with along with the blood sample by splitting a cross-sectional flow path in the channel at a first distal region thereof;
   an outer surface of the proximal end of the elongated body configured for operatively coupling the probe with a blood analyzer, whereby a blood sample may be drawn in through a proximal opening, through the channel and into the blood analyzer for analysis;
   the elongated body including
   a first set of apertures through the elongated body along a first transverse axis; and the elongate member including either
   a rod or wire material positioned through the first set of apertures resulting in the rod or wire material extending from the tip of the probe's elongated body and configured to reduce the cross sectional area of the probe tip, wherein the elongate member is contoured to catching clots and preventing the clots from being collected with along with the blood sample; and wherein
   the rod or wire material is attached to the elongated body at each of the apertures in the first set of apertures.

2. The probe of claim 1, wherein the primary opening is aligned with the longitudinal axis.

3. The probe of claim 1, wherein the elongated body is tubular.

4. The probe of claim 1, wherein the elongate member is configured to bisect the cross-sectional flow-path of the channel at the first distal region.

5. The probe of claim 1, further comprising at least one secondary opening to the channel defined through a side wall of the elongated body at a second distal region of the channel proximal to the first distal region.

6. The probe of claim 5, wherein the at least one secondary opening is defined along a second transverse axis perpendicular to the first transverse axis.

7. The probe of claim 1, wherein the at least one secondary opening is smaller than the primary opening.

* * * * *

UNITED STATES PATENT AND TRADEMARK OFFICE
CERTIFICATE OF CORRECTION

PATENT NO. : 10,837,955 B2
APPLICATION NO. : 15/861251
DATED : November 17, 2020
INVENTOR(S) : Roman Paz It is certified that error appears in the above-identified patent and that said Letters Patent is hereby corrected as shown below:

In the Claims

Claim 1, Column 2, Line 16 please replace the words "to catch" with the words "for catching".

Also:

Claim 1, Column 2, Line 33 please replace the word "to" with the word "for".

Signed and Sealed this
Third Day of September, 2024

Katherine Kelly Vidal
*Director of the United States Patent and Trademark Office*